United States Patent [19]

Trigger

[11] Patent Number: 4,970,202

[45] Date of Patent: Nov. 13, 1990

[54] PHARMACEUTICAL COMPOSITIONS CONTAINING NON-STEROIDAL ANTI-INFLAMMATORY DRUGS

[75] Inventor: David J. Trigger, Ashford, England

[73] Assignee: Delandale Laboratories Limited, Kent, England

[21] Appl. No.: 383,283

[22] Filed: Jul. 20, 1989

Related U.S. Application Data

[63] Continuation of Ser. No. 85,785, Aug. 17, 1987, abandoned.

[30] Foreign Application Priority Data

Aug. 18, 1986 [GB] United Kingdom ............... 86 20073

[51] Int. Cl.$^5$ ...................... A61K 31/40; A61K 31/60; A61K 31/615

[52] U.S. Cl. .................................... 514/159; 514/162; 514/408; 514/420

[58] Field of Search ................ 514/159, 720, 162, 408

[56] References Cited

PUBLICATIONS

Chem. Abst. (91)-117449y (1979).
Chem. Abst.(95)-126013m (1981).
Chem. Abst.(106)-149146S 1987.
Dayrene, P., et al., "Antiinflammatory and Immunostimulant Activities of Six Sulphur Compounds-Four Benzenesulphonates, Levamisole, and Pyritinol Hydrochloride Assayed In Mouse Cell Activation Studies," Arzneim-Forsch/Drug Res., 33, (I), 3 (1983), 372-377.
Dew, M. J., et al. "Maintenance Therapy for Duodenal Ulcer-a Trial Comparing Cimetidine with a Prostaglandin Synthetase Promoter." Journal of Clinical and Hospital Pharmacy, 9, (1984), 357-359.
Nagasubramanian, S. "The Effects of Ethamsylate and Calcium Dobesilate on the Outflow Facility and Intracular Pressure." Excerpta Medica I. C. S. (the Netherlands), 2/450 (1983), 1480-1484.
Extra Pharmacopoeia Martindale 28th Edition p736 (No. 1720p).
Extra Pharmacopoeia Martindale 28th Edition P1688 (No. 12506M).
Michal et al.: "Effect of Calcium Dobesilate and Its Interaction With Aspirin on Thrombus Formation In Vivo", Thrombosis Research, 40; 215-226, 1985.
Michielotto et al.: "Studio della coagulazione e dell-'emostasi in soggetti trattati con ciclonamina", Gazzetta Internazionale di Medicina e Chirurgia, Anno LXXI, vol. LXXII, No. 13, 1967.
Kotarba, Andrej: "Some Clinical Findings Relative to the Efficacity and Therapeutic Indications of a New Hemostatic: Dicynone", Acad. Med., Comm. Pers. Warsaw (1963).
Prato et al.: "Clinical Research and Experimental Findings on the Antihaemorrhagic Activity of Cyclohexadioenoline (Dicynene)", Minera Med., 59, Suppl. No. 28:1653-1657 (1968).
Esteve et al.: "Cyclonamine (141-E) et agents hemorragipares", Soc. Espanola Cienc. Fisiol., 5ieme Reunion Nationale, Madrid, Dec. 1959.
Whittle et al., "A Biochemical Basis for the Gastrointestinal Toxicity of Non-steroid Antirheumatoid Drugs", Arch. Toxicol., Supple. 7, 315-322 (1984). Toxicol.
Keat et al.: "Adverse GI Tract Reactions to Antirheumatic Drugs", Update, 15 Jun. 1985.
Dew: "Maintenance Therapy for Duodenal Ulcer-a Trial Comparing Cimetidine with a Prostaglandin Synthetase Promoter", Journal of Clinical and Hospital Pharmacy (1984) 9, 357-359.
Brooks et al.: "Non-Steroidal Anti-Inflammatory Drugs", Clinical Pharmacology of Anti-Inflammatory Compounds, Chapter 5, 59-85.
Hutton et al.: "Studies on the Action of Ethamsylate (Dicynene) on Haemostasis", Thrombosis and Haemostasis, 56(1), 6-8 (1986).

Primary Examiner—Stanley J. Friedman
Attorney, Agent, or Firm—Cushman, Darby & Cushman

[57] ABSTRACT

A pharmaceutical composition for treating an inflammatory condition contains a non-steroidal anti-inflammatory drug (NSAID) and a physiologically acceptable aromatic hydroxysulphonic acid. The two components may be for simultaneous, separate or sequential use. Administration of the two components, for example of aspirin with ethamsylate, reduces the damage which the NSAID does to the gastrointestinal tract while having no deleterious effect on the anti-inflammatory activity.

2 Claims, 1 Drawing Sheet

PHARMACEUTICAL COMPOSITIONS CONTAINING NON-STEROIDAL ANTI-INFLAMMATORY DRUGS

BACKGROUND OF THE INVENTION

The present invention relates to pharmaceutical compositions containing aspirin or other non-steroidal anti-inflammatory drugs (NSAIDs).

The non-steroidal anti-inflammatory drugs are a group of compounds which inhibit the biosynthesis of prostaglandins. The group embraces a wide range of chemical structures, but can be subdivided into several general structural types. These types are described in Chapter 5 of "The Clinical Pharmacology of Anti Inflammatory Compounds" by Brooks et al. One general type is based on a carboxylic acid structure while a second is based on enolic acid. Within the first general type are the aspirin-like NSAIDs, which have a structure based on salicylic acid and which include aspirin as well as diflunisal. Also within this general type are those compounds which are structurally related to propionic acid, such as naproxen and ibuprofen, and those related to acetic acid such as diclofenac and indomethacin. The second general type includes pyrazolones such as oxyphenbutazone and oxicams such as piroxicam.

NSAIDs have been extensively used in recent years for the treatment of chronic rheumatic or arthritic conditions and for the management of pain. The compounds are believed to bring relief by inhibiting prostaglandin synthetase at affected joints or in other body tissues. However, the compounds have recently been linked to increased occurrence of gastrointestinal blood loss resulting in anaemia and leading to peptic and duodenal ulcers in patients who use the drugs particularly over long time periods. These adverse reactions have been widely described, both in the press and in the scientific literature. For example, A. and E. Keat in an article in the June 1985 issue of "Update" described the adverse gastrointestinal tract reactions to antirheumatic drugs and in particular they mention that aspirin is known to be responsible for mucosal erosions, blood losses of around 5 ml per day, and for duodenal ulcers. B. J. R. Whittle and J. R. Vane in a paper, Arch. Toxicol, Suppl., 7, 315–322 (1984) considered the biochemical basis for the gastrointestinal toxicity of non-steroid antirheumatoid drugs and the effects of NSAIDs in inducing gastric damage.

In the shorter term, bleeding from the gastrointestinal tract is produced and gradual erosion of the gastric mucosa can lead to subsequent ulceration. These adverse effects on the gastrointestinal tract are believed to have two principal causes. Firstly many of the NSAIDs are chemical irritants which may annoy the gastric mucosa. Secondly, the NSAIDs inhibit prostaglandin synthesis not only in the joints but also, non-specifically, in the gut. Since some prostaglandins have a protective role in the gut, their absence makes the mucosa even more susceptible to damage by irritation.

In an attempt to overcome these drawbacks recent work has aimed at producing NSAIDs which have prostaglandin-like properties. These however have their own associated disadvantages in having secondary effects on smooth muscle activity.

The present inventors have discovered that by treatment with aspirin and an aromatic hydroxysulphonic acid in combination. gastrointestinal bleeding due to the aspirin can be significantly reduced, apparently without the introduction of further side effects.

Such aromatic hydroxysulphonic acids include ethamsylate (also known as cyclonamine). I, dobesilate calcium, II, and 263-E, III, which is the diethylamine salt of persilic acid. The formulae of these three compounds are shown below.

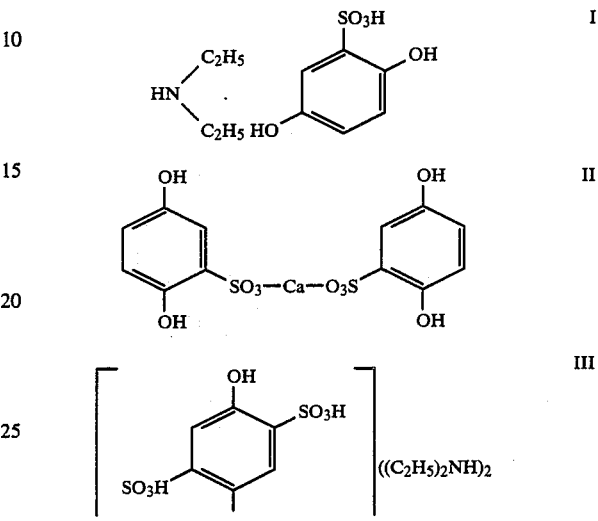

Ethamsylate is a known treatment for a variety of conditions where bleeding occurs from small blood vessels. For example, it has been used to control menorrhagia and bleeding during gynaecological surgery, to control haemorrhage during or after general surgery, to stop nose bleeds and control surgical haemorrhage in ear, nose and throat surgery and to limit or prevent periventricular haemorrhage in low birth weight babies. There have also been suggestions, based on qualitative observations, that ethamsylate may be a useful treatment for bleeding gastric ulcers. No use of ethamsylate in connection with iatrogenically induced bleeding has been mentioned.

The mode of action of ethamsylate is not well understood. Ethamsylate has been suggested to inhibit the operation of some prostaglandins. Work by the present inventors and others suggests that ethamsylate possibly has a selective inhibitory effect on prostaglandins $PGF_2$ alpha and $PGI_2$ (R. A. Hutton et al., Thrombosis and Haematosis 56, 6–8 (1986). The related compound 236-E is thought to be a prostaglandin synthetase promoter. Prostaglandins vary in their effects in the body, and a chemical which affects some prostaglandins in a particular manner may have a different or opposite effect on other prostaglandins.

The related compound, dobesilate calcium, is known to affect platelet aggregation and has been shown to inhibit artificially induced thrombus formation in hamster cheek pouches when administered by intraperitoneal injection (M. Michal et al, Thrombosis Research 40, 215–226 (1985). When the dobe-silate calcium was administered by injection in combination with aspirin a synergistic inhibition of thrombus formation was observed.

SUMMARY OF THE INVENTION

The present inventors have found, surprisingly, that by simultaneous administration of ethamsylate with the NSAID aspirin gastrointestinal bleeding induced by large doses of aspirin can be significantly reduced without there being any apparent effect on the prostaglandin-related anti-inflammatory activity of the NSAID. Reduction of gastric erosions in rats treated with indomethacin is also observed when the treatment is supplemented with ethamsylate.

According to one aspect of the present invention, there is provided a pharmaceutical product intended for treatment of a mammalian inflammatory condition containing a non-steroidal anti-inflammatory drug and a physiologically acceptable aromatic hydroxysulphonic acid, having on the aromatic nucleus one or more hydroxy groups and one or more sulphonic acid groups, or a salt thereof, said product being in the form of a combined preparation of said drug and said hydroxysulphonic acid or salt thereof for their simultaneous, separate, or sequential use in treatment of an inflammatory condition.

According to a further aspect of the present invention there is provided a method of treatment of an inflammatory condition in a mammal comprising administering to said mammal a non-steroidal anti-inflammatory drug and further administering an aromatic hydroxysulphonic acid or salt thereof in an amount and at a time so as to inhibit gastrointestinal bleeding caused by said drug.

Preferably the aromatic nucleus is a benzene ring. Preferably there are two hydroxy groups whose positions of substitution on the aromatic nucleus are separated by two carbon atoms. In the case where the nucleus is a benzene ring the hydroxy groups are therefore preferably at ortho and meta positions to the sulphonic or sulphonate group. There may be two sulphonic acid or sulphonate groups, or one sulphonic acid or sulphonate group and one or more —$SO_3R$ groups where R is alkyl or substituted alkyl. Particularly preferred compounds are ethamsylate, dobesilate calcium and 263-E.

Preferred non-steroidal anti-inflammatory drugs include:

| ASPIRIN LIKE: | aspirin |
| --- | --- |
| | diflunisal |
| PROPIONIC ACID TYPE: | ibuprofen |
| | naproxen |
| | ketoprofen |
| | fenoprofen |
| | flurbiprofen |
| | fenbufen |
| | benoxaprofen |
| | tiaprofenic acid |
| | indoprofen |
| | suprofen |
| OTHER: | |
| PYRANOCARBOXYLATES: | etodolac |
| ACETIC ACID TYPE: | zomepirac |
| | indomethacin |
| | alclofenac |
| | sulindac |
| | fenclofenac |
| | diclofenac |
| | tolmetin |
| FENAMIC ACIDS: | mefanamic acid |
| PYRAZOLONES: | phenylbutazone |
| | oxyphenbutazone |
| | azapropazone |
| | feprazone |
| OXICAMS: | piroxicam |

The formulation may be made up with suitable pharmaceutical carrier material in any suitable form for administration to a patient, preferably oral administration. If in tablet or capsule form, the amount of NSAID may be equal to the desired daily dose or to a fraction thereof. The active ingredients may be intimately mixed or if necessary separated from each other e.g. as a mix of coated crystals, for reasons of physico-chemical incompatiblity. The active ingredients may even be in separate dosage forms, e.g. separate tablets, and presented in a suitable package with instructions for administration. Sequential administration may be arranged.

The amount of the non-steroidal anti-inflammatory drug which is included in the formulation depends on the particular NSAID which is to be incorporated. Preferably, the weight ratio of the NSAID to the aromatic hydroxysulphonic acid or salt thereof is not less than 0.02. In view of the widely differing activities of the various NSAIDs a more appropriate way of expressing the ratio is in terms of aspirin equivalents. One aspirin equivalent is the mass of NSAID which has the same activity as 1 g of aspirin. On this basis, the preferred weight ratio of NSAID (expressed as aspirin equivalents) to the aromatic hydroxysulphonic acid or salt thereof is not less than 0.1. Where the NSAID is aspirin, the daily dose may be between 1 and 10 g preferably 2 to 4 g and more preferably about 2.5 g. For the other NSAIDs mentioned above suitable daily doses are as follows (the amount of NSAID in one aspirin equivalent is indicated in brackets):

| | |
| --- | --- |
| diflusinal | 250–2000 mg, preferably 250–1000 mg; (250 mg); |
| ibuprofen | 200–3600 mg, preferably 200–1800 mg; (200 mg); |
| naproxen | 250–2000 mg, preferably 250–1000 mg; (250 mg); |
| ketoprofen | 50–400 mg, preferably 50–200 mg; (50 mg); |
| fenoprofen | 300–4800 mg, preferably 300–2400 mg; (300 mg); |
| flurbiprofen | 50–400 mg, preferably 50–200 mg; (50 mg); |
| fenbufen | 300–1800 mg, preferably 300–900 mg; (300 mg); |
| benoxaprofen | 100–1200 mg, preferably 100–600 mg; (100 mg); |
| tiaprofenic acid | 200–1200 mg, preferably 200–600 mg; (200 mg); |
| indoprofen | 100–1600 mg, preferably 100–800 mg; (100 mg); |
| suprofen | 200–1600 mg, preferably 200–800 mg; (200 mg). |
| etodolac | 200–1200 mg, preferably 200–600 mg; (200 mg). |
| zomepirac | 100–1200 mg, preferably 100–600 mg; (100 mg); |
| indomethacin | 25–400 mg, preferably 25–200 mg; (25 mg); |
| alclofenac | 500–6000 mg, preferably 500–3000 mg; (500 mg); |
| sulindac | 100–800 mg, preferably 100–400 mg; (100 mg); |
| fenclofenac | 300–2400 mg, preferably 300–1200 mg; (300 mg); |
| diclofenac | 25–300 mg, preferably 25–150 mg; (25 mg); |
| tolmetin | 200–3600 mg, preferably 200–1800 mg; (200 mg); |
| mefanamic acid | 25–3000 mg, preferably 25–1500 mg; (25 mg); |
| phenylbutazone | 100–1200 mg, preferably 100–1200 mg; (100 mg); |
| oxyphenbutazone | 25–400 mg, preferably 25–200 mg; (25 mg); |
| azapropazone | 300–4800 mg, preferably 300–2400 mg; (300 mg); |
| feprazone | 200–1200 mg, preferably 200–600 mg; (200 mg); |
| piroxicam | 10–80 mg, preferably 10–40 mg; (10 mg); |

When ethamsylate is included as the aromatic hydroxysulphonic acid component of the composition, a preferred daily dose is between 250 mg and 4 g. Preferably about 2 g per day is included. Preferred daily dose ranges of dobesilate and of 263E are about 125 mg–3 g, and about 250 mg–3 g respectively, and suitable examples are 750 mg and 1500 mg respectively.

A preferred weight ratio range for aspirin/ethamsylate is 40:1 to 1:4, more preferably 10:1 to 1:2. When aspirin and dobesilate calcium are employed as NSAID and aromatic hydroxysulphonic acid salt the weight ratio is preferably from 80:1 to 1:3. more preferably 20:1 to 1:2. Preferred weight ratio ranges for the other NSAIDs listed above can be calculated from the daily dosage ranges given above and the preferred daily dosage range of 250 mg to 4 g for ethamsylate, and those for the other aromatic hydroxysulphonic acids.

Figure 1:
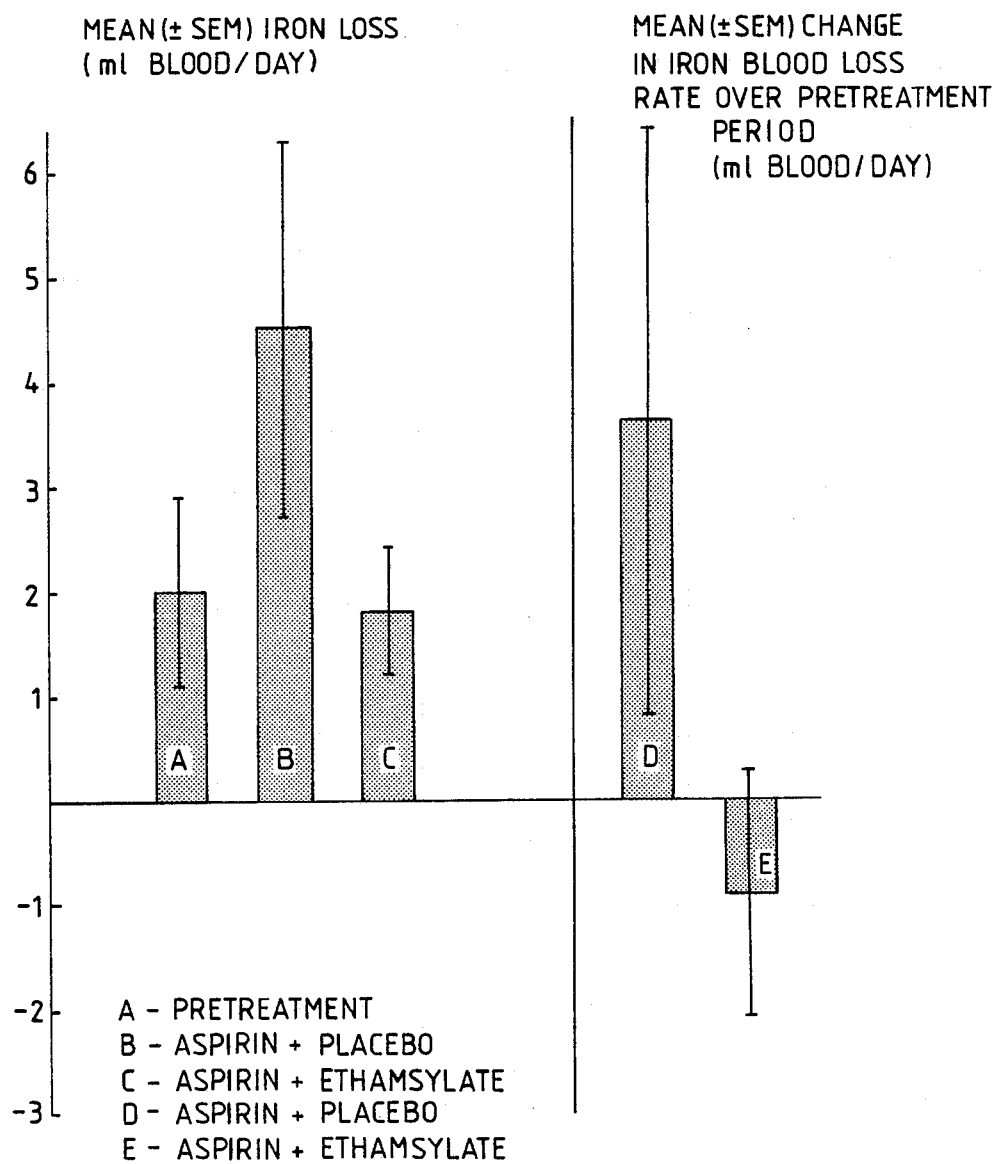
FIG. 1 shows a histogram of blood loss in ml blood/day from the gastrointestinal tract of patients who were dosed with aspirin placebo or aspirin+ethamsylate.

A. shows mean rate of blood loss over pretreatment period

B. shows mean rate of blood loss in patients treated with aspirin+placebo

C. shows mean rate of blood loss in patients treated with aspirin+ethamsylate

D. and E. show the change in iron blood loss rate compared with the pretreatment period for volunteers given aspirin+placebo, or aspirin+ethamsylate respectively.

DESCRIPTION OF THE PREFERRED EMBODIMENTS

Examples

The present inventors have investigated the effect of ethamsylate on increased capillary bleeding time and blood loss brought about by aspirin administration in humans and also the effect of ethamsylate on aspirin-induced gastric bleeding in humans.

The inventors have also carried out studies in animals to investigate the effect of ethamsylate in reducing gastrointestinal damage due to the administration of NSAID and to monitor the effect of ethamsylate on the beneficial effects of the NSAID at an inflamed joint. The effect of the NSAID, indomethacin, with and without ethamsylate, on the gastrointestinal tract of rats was also investigated. These experiments are described below.

EXAMPLE 1

Twelve normal healthy subjects (six males, six females, mean age 31.4 years, range 22 to 45 years) were entered into a randomised, double blind trial which involved two 48 hour treatment periods (one with placebo and one with the active compound) separated by a 12 day recovery period. None of the subjects ingested any drugs known to interfere with platelet aggregation during or in the two weeks preceding the trial. In addition, alcoholic beverages were excluded for at least 48 hours prior to each treatment period. The following protocol was used for each subject and for each treatment period. At 9 to 10 a.m. on day 1 a template bleeding time test was performed. Immediately following sampling, treatment period A commenced with either ethamsylate (1×500 mg tablet, by mouth, four times daily) or placebo (matched, inert tablets, by mouth, four times daily) and continued for 48 hours. 24 hours after commencing treatment the bleeding time test was repeated and the second blood sample was collected as before. Aspirin (600 mg. soluble, by mouth) was then administered. Two hours later a further bleeding time test was performed and this was repeated, along with collection of the third blood sample, 24 hours after aspirin.

After a recovery period of 12 days, treatment B commenced, the protocol being identical to treatment A except that subjects given placebo in the first period now received ethamsylate and vice versa.

Template bleeding time tests were performed using the Simplate II device (General Diagnostics). All blood emerging from the wounds was absorbed on to Whatman No. 1 filter papers. Subsequently the blood was eluted into ammoniated water and, after centrifugation at 2000 g for 20 minutes, the optical density was measured in a spectrophotometer at 540 nm.

The results of the experiments are shown in Table 1. It may be seen from Table 1 that ethamsylate has the effect of reducing both the duration of bleeding when aspirin is administered with placebo from a recorded increase of 3.25 minutes (equivalent to 52% increased on basal value) to 1.73 minutes (equivalent to 28% increase on basal value) and the amount of blood loss from an increase of 0.721 ml (equivalent to 187% increase) to only 0.277 ml (equivalent to 72% increase). The effects illustrated by both of these results are statistically significant and represent an approximate halving of the effects of aspirin in increasing bleeding time and blood loss by the dose of the ethamsylate used.

On the basis that this type of experiment can be used as a model for bleeding from the gastrointestinal tract, the results indicate the beneficial effects which can be expected if a NSAID is combined with ethamsylate or similar compound.

TABLE 1
EFFECT OF ETHAMSYLATE ON THE BLEEDING TIME

|     | Duration of bleeding (min) | | Blood loss (OD units) | |
| --- | --- | --- | --- | --- |
|     | Placebo | Ethamsylate | Placebo | Ethamsylate |
| (A) | 6.21 ± 0.54 | | 0.385 ± 0.047 | |
| (B) | 6.46 | 5.52 | 0.573 | 0.318 |
|     | ±0.80 | ±0.46 | ±0.187 | ±0.053 |
| (C) | 9.46* | 7.94 | 1.106$ | 0.662 |
|     | ±0.96 | ±0.77 | ±0.236 | ±0.134 |

Results expressed as mean ± SEM
(A) = Basal
(B) = After 24 hour treatment
(C) = Post aspirin
* p = 0.003 compared to basal,
$ p = 0.006 compared to basal using Mann-Whitney test.

EXAMPLE 2

Experiments in a group of twelve human volunteers have shown the advantageous effect of administering aspirin in conjunction with ethamsylate in order to reduce the increase in blood loss connected with aspirin administration. Five volunteers took two 300 mg aspirin tablets and one placebo tablet four times a day. Thus the total daily dose was 12 tablets containing a total of 2400 mg of aspirin. The other seven volunteers consumed two 300 mg aspirin tablets and one tablet containing 500 mg of ethamsylate four times daily. Thus they consumed a total of 12 tablets having 2400 mg aspirin and 2000 mg of ethamsylate in total. Before treatment with the aspirin was commenced each patient was given an injection of 10 microcuries of $^{59}$Fe in order that his red blood cells were radioactively labelled and blood loss from the gut could be monitored by monitoring the change in radioactivity of each volunteer. Whole body counts were performed immediately before and after the isotope injection and also at 7,14,2 and 28 days after the injection in order to obtain a measure of the daily blood loss in the absence of aspirin. Patients then started a 21 day course of tablets and whole body counts were repeated on day 36,42,49 and 56 from the initial isotope injection (Day 1). In each case an additional blood sample was taken on day 42, to calibrate faecal blood loss for haematological and biochemical specimens and for determination of plasma aspirin and ethamsylate levels.

Mean blood losses in millilitres per day before and after aspirin plus placebo or aspirin plus ethamsylate treatment for the twelve patients are shown in Table 2.

The effect of ethamsylate is very clear. The results are presented as a histogram in FIG. 1. In the FIGURE iron loss is expressed as ml blood/day during:

A, a pretreatment period;
B, treatment with aspirin and placebo;
C, treatment with aspirin and ethamsylate;

the mean change in blood loss rate compared with the pretreatment pretreatment period are shown at D and E. It can be seen that the daily blood loss from those volunteers taking aspirin, but not taking ethamsylate is four times higher than that of volunteers who were receiving ethamsylate as well as aspirin.

TABLE 2

ASPIRIN/ETHAMSYLATE VOLUNTEER BLOOD LOSS STUDY

| | MEAN IRON LOSS RATE (ML BLOOD/DAY) | | INCREASE IN IRON LOSS RATE OVER PRETREATMENT PERIOD (ML BLOOD/DAY) | |
|---|---|---|---|---|
| PRETREATMENT PERIOD | ASPIRIN + PLACEBO | ASPIRIN + ETHAMSYLATE | ASPIRIN + PLACEBO | ASPIRIN + ETHAMSYLATE |
| +2.0 ± 0.9* | +4.5** ± 1.8* | +1.8** ± 0.6* | +3.6 ± 2.8* | −0.9 ± 1.2* |
| * = SEM | * = SEM | * = SEM | * = SEM | * = SEM |
| N = 12 | N = 5 | N = 7 | N = 5 | N = 7 |
| | **INCREASE OVER PRETREATMENT VALUE, SIGNIFICANT AT 95% LEVEL (WILCOXSON) | **NOT SIGNIFICANT VS PRETREATMENT OR ASPIRIN + PLACEBO | | |

EXAMPLE 3

Rats were dosed as indicated below in table 3. Aspirin, or aspirin together with ethamsylate was administered by mouth.

The rats were killed by cervical dislocation three hours after administration of the test materials and the stomachs were dissected out. The stomachs were opened by a medical incision round the greater curvature and pinned onto a dissecting board. Gastric erosions including ulcers were assessed and numbers counted. Lesions greater than 9 mm$^2$ were recorded separately.

The results were as shown in Table 3 below:

TABLE 3

MEAN GASTRIC EROSION SCORES OF RATS TREATED WITH ETHAMSYLATE AND/OR ASPIRIN

| Aspirin (mg/kg by mouth) | Ethamsylate (mg/kg by mouth) | Mean gastric erosion scores | | | |
|---|---|---|---|---|---|
| | | Focal Lesions | Intermediate Lesions | Gross Lesions | Total |
| 150 | — | 3.0 | 1.2 | 0.0 | 4.2 |
| 300 | — | 24.4 | 2.1 | 0.0 | 26.5 |
| 150 | 250 | 0.5 | 0.0 | 0.0 | 0.5 |
| 300 | 250 | 1.7 | 0.5 | 0.0 | 2.2 |

Ethamsylate significantly reduced the numbers of gastric erosions seen at terminal autopsy.

EXAMPLE 4

Rats were dosed by mouth employing aspirin as NSAID. Doses of aspirin and of ethamsylate used are given in Table 4. Thirty minutes after the test materials had been administered each rat was given an injection, in one paw, of 0.1 ml of a 1% solution of sodium carrageenin in saline. Paw volumes were measured at one, two and three hours thereafter.

The rat paw oedema model was selected for assessing the effects of ethamsylate on the anti-inflammatory activity of aspirin because it gives a quantitative measure of activity which can be used to assess relative potency more readily than other short term anti-inflammatory test procedures. The results are shown in Table 4 and are typical, with a dose-related slowing of the swelling induced by the carrageen.

TABLE 4

MEAN CARRAGEEN INFLAMED PAW VOLUMES OF RATS TREATED WITH ETHAMSYLATE AND/OR ASPIRIN

| Aspirin (mg/kg) | Ethamsylate (mg/kg) | Mean body weight (g) (+ s.e.m.) | Paw volume (arbitary units) ± s.e.m. | | | |
|---|---|---|---|---|---|---|
| | | | Pretreatment | 1 hr | 2 hr | 3 hr |
| 150 | — | 95.8 (1.52) | 32.9 (1.10) | 43.0 (0.94) | 52.0 (1.58) | 56.1 (1.00) |
| 300 | — | 91.4 (1.38) | 37.2 (1.04) | 43.5 (0.79) | 44.0 (0.83) | 47.9 (0.85) |
| 150 | 250 | 94.5 (2.17) | 34.4 (1.38) | 43.7 (1.10) | 48.1 (1.45) | 50.9 (1.78) |
| 300 | 250 | 91.8 (1.55) | 35.8 (0.84) | 41.5 (0.78) | 44.5 (1.02) | 46.0 (1.16) |
| — | — | 92.9 (1.42) | 35.0 (1.35) | 47.1 (1.37) | 56.8 (1.81) | 60.6 (1.18) |

Ethamsylate does not significantly affect the inhibition, by of paw swelling at either dose level used. Analysis of variance was carried out on the 3-hour data and confirmed that the concurrent administration of ethamsylate caused no significant change in the potency of aspirin. Relative potency of aspirin ethamsylate compared to aspirin alone was 1.45 (95% fiducial limits 0.97–2.18).

It is concluded from examples 3 and 4 that ethamsylate does not inhibit the anti-inflammatory activity of aspirin although it does significantly reduce gastric erosions induced by aspirin.

EXAMPLE 5

In this example the extent of duodenal damage was assessed using the inflation method described by E. Ezer et al J. Pharm. Pharmacol. (1975)27, 866. One group of rats was given indomethacin daily by mouth, at a dose of 30 mg/kg while a second group received the same dose of indomethacin in combination with 250 mg/kg ethamsylate. This technique then involved inflating the isolated duodenum with physiological saline and recording the pressure at which the intestinal wall ruptured. The recorded pressure of rupture gives an indication of the tensile strength of the gut and therefore a measure of the ulcerative damage.

The mean duodenal rupture pressure for rats which had been dosed with 30 mg/kg indomethacin for 2 days and sacrificed on day 3 was 38±21 mm Hg, while for rats dosed also with ethamsylate the mean rupture pressure was 70±35 mm Hg.

Thus, it can be seen that ethamsylate provided protection, in that the intestinal strength was greater (or rupture pressure was increased) when ethamsylate was administered concurrently with indomethacin.

An additional indication of the protective effect of ethamsylate was given by comparative mortality figures on continuation of dosing, as shown in Table 5.

TABLE 5

|  | Day of experiment | | | | |
| --- | --- | --- | --- | --- | --- |
|  | 1 | 2 | 3 | 4 | 5 |
| Indomethacin/Gum Acacia, % survival = | 100 | 100 | 90 | 40 | 20 |
| Indomethacin/Ethamsylate, % survival = | 100 | 100 | 100 | 80 | 60 |

It can be seen that three times as many animals survive to 5 days when the combination is given.

For the animals that had been dosed for 4 days and survived to day 5, the duodenal rupture pressures were 2.5 mm Hg for those rats which were dosed at 30 mg/kg of indomethacin and 113±52 mm Hg for rats dosed with 30 mg/kg of indomethacin and 250 mg/kg ethamsylate.

These results show that ethamsylate exerts a protective effect against gastrointestinal damage caused by indomethacin.

I claim:

1. A pharmaceutical product intended for treatment of a mammalian inflammatory condition and for inhibiting gastro-intestinal bleeding associated with said treatment, said product containing a non-steroidal anti-inflammatory drug selected from the group consisting of aspirin, tolmetin and indomethacin, and also ethamsylate of formula I,

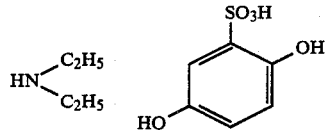

in an amount so as to inhibit said gastro-intestinal bleeding, said product being in the form of a combined preparation of said drug and ethamsylate for their simultaneous, separate, or sequential use in said treatment of an inflammatory condition.

2. Method of treatment of inflammatory condition in a mammal and of inhibiting gastrointestinal bleeding associated with said treatment said method comprising administering to said mammal a non-steriodal anti-inflammatory drug selected from the group consisting of aspirin, indomethacin, and tolmetin and further administering ethamsylate in an amount and at a time so as to inhibit said gastrointestinal bleeding caused by said drug.

* * * * *